(12) United States Patent
Soma et al.

(10) Patent No.: US 8,940,777 B2
(45) Date of Patent: Jan. 27, 2015

(54) PEST CONTROLLING COMPOSITION AND METHOD OF CONTROLLING PEST

(75) Inventors: Masato Soma, Narashino (JP); Atsushi Iwata, Takarazuka (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 0 days.

(21) Appl. No.: 13/130,781

(22) PCT Filed: Nov. 20, 2009

(86) PCT No.: PCT/JP2009/070066
§ 371 (c)(1),
(2), (4) Date: Jul. 19, 2011

(87) PCT Pub. No.: WO2010/061934
PCT Pub. Date: Jun. 3, 2010

(65) Prior Publication Data
US 2011/0263586 A1 Oct. 27, 2011

(30) Foreign Application Priority Data
Nov. 25, 2008 (JP) .................. 2008-299274

(51) Int. Cl.
*A01N 43/88* (2006.01)
*A01N 57/02* (2006.01)

(52) U.S. Cl.
CPC .................................. *A01N 57/02* (2013.01)
USPC .................. 514/365; 514/341; 514/229.2

(58) Field of Classification Search
CPC ....... A01N 57/02; A01N 43/40; A01N 47/40; A01N 51/00; A01N 2300/00
USPC .................. 514/365, 341, 229.2
See application file for complete search history.

(56) References Cited

U.S. PATENT DOCUMENTS

| 4,628,049 A | 12/1986 | Kato |
| 2007/0093391 A1 | 4/2007 | Fischer et al. |
| 2008/0113940 A1 | 5/2008 | Erdelen et al. |
| 2009/0143447 A1 * | 6/2009 | Arthur et al. .................. 514/370 |

FOREIGN PATENT DOCUMENTS

| CN | 1190870 A | 8/1998 |
| CN | 1209727 A | 3/1999 |
| CN | 1228256 | * 9/1999 |
| DE | 19519007 A1 | 11/1996 |
| JP | 2008-156301 A | 7/2008 |
| TW | 200838425 A | 10/2008 |
| WO | WO 96/03879 A1 | 2/1996 |
| WO | WO 2006/024333 A2 | 3/2006 |
| WO | WO 2009/073164 A1 | 6/2009 |

OTHER PUBLICATIONS

Derwent Abstract for CN 1228256.*
Machine Translation for CN 1228256.*
Guotong Chi (Chinese Application Publication CN 1228256)—Certified translation.*
International Preliminary Report on Patentability and the Written Opinion of the International Searching Authority dated Jun. 9, 2011 for Application No. PCT/JP2009/070066 (Forms PCT/IB/326, PCT/IB/373, and PCT/ISA/237).
International Search Report, dated May 6, 2010 in PCT/JP2009/070066.
Ed. Tomun, "The Pesticide Manual," Fourteenth Edition, ISBN 1 901396 14 2, pp. 209-210; 598-599: 1022-1023; 1043-1044, 2006, British Corp Production Council.
First Office Action for corresponding Chinese Patent Application No. 200980147079.8, dated Nov. 22, 2012.
Office Action for corresponding Colombian Patent Application No. 11 063127, dated Dec. 18, 2012.
English translation of Japanese Office Action dated May 28, 2013 for Application No. 2008-299274.
Extended European Search Report for European Application No. 13169407.7 dated Sep. 5, 2013.
The Third Office Action (including English translation), dated Mar. 7, 2014, issued in the corresponding Chinese Patent Application No. 200980147079.8.
The Office Action (including English translation), dated Jan. 15, 2014, issued in the corresponding Taiwanese Patent Application No. 098138106.
Chinese Office Action for corresponding Application No. 200980147079.8 dated Jul. 22, 2013 (with English translation).
Russian Office Action for corresponding Application No. 2011126203/13 dated Aug. 15, 2013 (with English translation).
The Patent Examination Report No. 1, dated Jun. 11, 2014, issued in the corresponding Australian Patent Application No. 2009320713.
The Office Action, dated Oct. 17, 2014, issued in the corresponding Philippine Patent Application No. 1/2011/501025.

* cited by examiner

*Primary Examiner* — Sean Basquill
(74) *Attorney, Agent, or Firm* — Birch, Stewart, Kolasch & Birch, LLP

(57) ABSTRACT

A pest controlling composition comprising tolclofos-methyl and a neonicotinoid compound represented by the formula (1) as active ingredients.

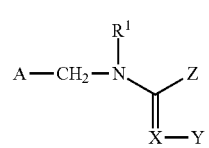

(1)

6 Claims, No Drawings

PEST CONTROLLING COMPOSITION AND METHOD OF CONTROLLING PEST

TECHNICAL FIELD

The present invention relates to a pest controlling composition and a method of controlling a pest.

BACKGROUND ART

Conventionally, as an active ingredient of a pest controlling composition, neonicotinoid compounds having an insecticidal activity and tolclofos-methyl having a disinfecting activity are known (see, The Pesticide Manual—14th edition, published by BCPC, ISBN 1901396142, e.g. page 209, page 1022, page 598, page 1043).

DISCLOSURE OF THE INVENTION

The present invention has an object of providing a pest controlling composition having an excellent controlling effect against a pest, a method of controlling a pest, and the like.

The present inventors have intensively studied and resultantly found that a controlling effect against pests is improved by use of tolclofos-methyl together with a neonicotinoid compound of the following formula (1), which led to attain the present invention.

The present application is related to the following inventions:

[1] A pest controlling composition comprising tolclofos-methyl and a neonicotinoid compound represented by the formula (1) as active ingredients:

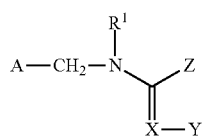

(1)

wherein A represents a 6-chloro-3-pyridyl group, a 2-chloro-5-thiazolyl group, a tetrahydrofuran-2-yl group or a tetrahydrofuran-3-yl group, Z represents a methyl group, an $NHR^2$ group, an $N(CH_3)R^2$ group or an $SR^2$ group, $R^1$ represents a hydrogen atom, a methyl group or an ethyl group, $R^2$ represents a hydrogen atom or a methyl group, or $R^1$ and $R^2$ together represents a $CH_2CH_2$ group or a $CH_2OCH_2$ group, X represents a nitrogen atom or a CH group, and Y represents a cyano group or a nitro group.

[2] The pest controlling composition according to [1], wherein the neonicotinoid compound is selected from the group consisting of clothianidin, imidacloprid and thiamethoxam.

[3] The pest controlling composition according to [1] or [2], wherein the weight ratio of tolclofos-methyl to the neonicotinoid compound is in the range of 0.002:1 to 500:1.

[4] A seed treating composition comprising tolclofos-methyl and the neonicotinoid compound as active ingredients.

[5] A plant seed treated with an effective amount of tolclofos-methyl and the neonicotinoid compound.

[6] A pest controlling method which comprises applying tolclofos-methyl and the neonicotinoid compound as active ingredients to a pest, a plant or a soil for cultivating the plant.

[7] Use of a combination of tolclofos-methyl and the neonicotinoid compound for controlling a pest.

BEST MODES FOR CARRYING OUT THE INVENTION

Tolclofos-methyl is a known compound, which is described in, for example, "The Pesticide Manual 14th edition, published by BCPC, ISBN 1901396142". This compound is obtained from commercially available preparations or produced by known methods.

The neonicotinoid compound in the present invention is represented by the formula (1):

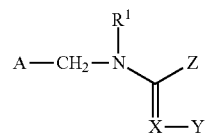

(1)

In the formula (1),

A represents a 6-chloro-3-pyridyl group, a 2-chloro-5-thiazolyl group, a tetrahydrofuran-2-yl group or a tetrahydrofuran-3-yl group. A preferably represents a 6-chloro-3-pyridyl group or a 2-chloro-5-thiazolyl group.

Z represents a methyl group, an $NHR^2$ group, an $N(CH_3)R^2$ group or an $SR^2$ group.

$R^1$ represents a hydrogen atom, a methyl group or an ethyl group.

$R^2$ represents a hydrogen atom or a methyl group. $R^1$ and $R^2$ may together represent a $CH_2CH_2$ group or a $CH_2OCH_2$ group. $R^2$ preferably represents a hydrogen atom, or a $CH_2CH_2$ or $CH_2OCH_2$ group together with $R^1$.

X represents a nitrogen atom or a CH group. X preferably represents a nitrogen atom.

Y represents a cyano group or a nitro group.

The neonicotinoid compound is a known compound, which is described in, for example, "The Pesticide Manual 14th edition, published by BCPC, ISBN 1901396142". These compounds are produced by known methods and commercially available.

Specific examples of the neonicotinoid compound represented by the formula (1) include:

a compound in which A represents a 2-chloro-5-thiazolyl group, Z represents an $NHCH_3$ group, $R^1$ represents a hydrogen atom, X represents a nitrogen atom and Y represents a nitro group (generic name: clothianidin), a compound in which A represents a 2-chloro-5-thiazolyl group, Z represents an $N(CH_3)R^2$ group, $R^1$ represents a $CH_2OCH_2$ group together with $R^2$, X represents a nitrogen atom and Y represents a nitro group (generic name; thiamethoxam), a compound in which A represents a 6-chloro-3-pyridyl group, Z represents an $NHR^2$ group, $R^1$ represents a $CH_2CH_2$ group together with $R^2$, X represents a nitrogen atom and Y represents a nitro group (generic name: imidacloprid), a compound in which A represents a 6-chloro-3-pyridyl group, Z represents an $N(CH_3)R^2$ group, $R^1$ represents an ethyl group, $R^2$ represents a hydrogen atom, X represents a CH group and Y represents a nitro group (generic name: nitenpyram), a compound in which A represents a tetrahydrofuran-3-yl group, Z represents an $N(CH_3)R^2$ group, $R^1$ represents a hydrogen atom, $R^2$ represents a hydrogen atom, X represents a nitrogen atom and Y represents a nitro group (generic name: dinotefuran), a compound in which A represents a 6-chloro-3-pyridyl group, Z represents a methyl group, $R^1$ represents a methyl group, X represents a nitrogen atom and Y represents a cyano group (generic name: acetamiprid), and a compound in which A represents a 6-chloro-3-pyridyl group, Z represents an $SR^2$ group, $R^1$ represents a $CH_2CH_2$ group together with $R^2$, X represents a nitrogen atom and Y represents a cyano group (generic name: thiacloprid).

Among them, clothianidin, thiamethoxam and imidacloprid are preferable, and clothianidin is more preferable.

In the pest controlling composition according to the present invention, the weight ratio of tolclofos-methyl to the neonicotinoid compound (=tolclofos-methyl:neonicotinoid compound) is in the range of usually 0.002:1 to 500:1, preferably 0.004:1 to 100:1.

When the composition is used as a spraying agent, the weight ratio is more preferably in the range of 0.025:1 to 40:1. When the composition is used as a seed treating composition, the weight ratio is more preferably in the range of 0.01:1 to 100:1.

Although the pest controlling composition according to the present invention can be obtained by simply mixing tolclofos-methyl and a neonicotinoid compound represented by the formula (1), it is usually obtained by mixing tolclofos-methyl, the neonicotinoid compound and an inert carrier, adding if necessary a surfactant and other auxiliary agents for formulation, and formulating into a formulation such as oil solution, emulsifiable concentrate, flowable, wettable powder, granulated wettable powder, dust and granules. The formulation can be carried out by conventionally known procedures.

In the pest controlling composition according to the present invention, the total amount of tolclofos-methyl and the neonicotinoid compound is in the range of usually 0.1 to 99 wt %, preferably 0.2 to 90 wt %.

The inert carrier includes solid carriers and liquid carriers.

The solid carriers are in the form of fine powder, particle and the like. Examples of the materials thereof include minerals such as kaolin clay, attapulgite clay, bentonite, montmorillonite, acid white clay, pyrophyllite, talc, diatomaceous earth or calcite; natural organic substances such as corn cob powder or walnut shell powder; synthetic organic substances such as urea; inorganic salts such as calcium carbonate or ammonium sulfate; synthetic inorganic substances such as synthetic hydrated silicon oxide.

Examples of the liquid carriers include aromatic hydrocarbons such as xylene, alkylbenzene or methylnaphthalene; alcohols such as 2-propanol, ethylene glycol, propylene glycol or ethylene glycol monoethyl ether; ketones such as acetone, cyclohexanone or isophorone; vegetable oils such as soybean oil or cotton seed oil; petroleum aliphatic hydrocarbons; esters; dimethyl sulfoxide; acetonitrile; and water.

Examples of the surfactant include anionic surfactants such as an alkyl sulfate, alkyl aryl sulfonate, dialkyl sulfosuccinate, polyoxyethylene alkyl aryl ether phosphate, lignin sulfonate, or naphthalene sulfonate formaldehyde polycondensate; nonionic surfactants such as a polyoxyethylene alkyl aryl ether, polyoxyethylene alkyl polyoxypropylene block copolymer or sorbitan fatty ester; and cationic surfactants such as an alkyl trimethyl ammonium salt.

Examples of the other auxiliary agents for formulation include water-soluble polymers such as polyvinyl alcohol, or polyvinyl pyrrolidone; polysaccharides such as gum Arabic, alginic acid and salts thereof, CMC (carboxymethylcellulose) or xanthan gum; inorganic substances such as aluminum magnesium silicate or alumina sol; antiseptic agents; coloring agents; and stabilizers such as PAP (acidic isopropyl phosphate) or BHT.

The pest controlling method of the present invention comprises applying tolclofos-methyl and the neonicotinoid compound represented by the formula (1) as active ingredients to a pest, a plant or a soil for cultivating the plant.

Examples of the pest include harmful arthropods such as mites or harmful insects, nemathelminths, mollusks, and microorganisms such as molds causing plant diseases. Specific examples of the pests will be described later.

By applying an effective amount of tolclofos-methyl and the neonicotinoid compound to the pest, the plant or a soil for cultivating the plant according to the controlling method, it can be realized not only to control a pest but also to protect a plant from offense by a pest.

In the present invention, the "effective amount" means an amount of the sum of tolclofos-methyl and the neonicotinoid compound. It includes such an amount that one of the compounds are less than the amount which cannot show its effect in case of using only the one.

The plant includes plant stems and leaves, plant seeds, plant bulbs. Here, the bulb means a scaly bulb, solid bulb, root stock, stem tuber, root tuber and rhizophore.

In the controlling method of the present invention, tolclofos-methyl and a neonicotinoid compound represented by the formula (1) are usually applied in the form of the pest controlling composition of the present invention because of easiness of application. These compounds may also be separately applied in the same period. The present application also includes use of a combination of tolclofos-methyl and the neonicotinoid compound for controlling a pest.

The controlling method of the present invention includes specifically a treatment of plant stems and leaves such as spraying onto stems and leaves, a treatment of plant cultivation land such as a soil treatment, a treatment of seeds such as seed sterilization, seed coat, a treatment of bulbs such as seed tuber, and other treatments.

The treatment of plant stems and leaves specifically include treatment methods which comprise applying compounds onto the surface of plants, e.g. application onto stems and leaves, or application onto trunk.

Examples of the soil treatment method include application onto a soil, mixing with a soil, drenching a soil with a chemical solution (chemical solution irrigation, soil injection, chemical solution drip).

The soil treatment is performed on the soil of a planting hole, planting row, a planting hole, a planting row, the whole surface of plantation, culm base parts, planting interval, lower parts of trunk, main path, cultivation soil, seedling raising box, seedling raising tray or seedbed.

The soil treatment can appropriately be performed before sowing, in sowing, directly after sowing, in seedling raising period, before fix planting, in fix planting, in growing period after fix planting.

In the soil treatment, a solid fertilizer such as a paste fertilizer containing the active ingredient may be applied to a soil. The soil treatment may also be carried out by application of an irrigation solution mixed with the active ingredient, such application as injection into an irrigation equipment (e.g., irrigation tube, irrigation pipe, sprinkler), mixing into an interrow solution, mixing into a hydroponic solution or a spraying treatment.

Examples of the treatment of a seed include a spray treatment which comprises spraying a suspension of the pest controlling composition of the present invention in the form of mist onto the surface of a seed or the surface of a bulb, a coating treatment which comprises coating the pest controlling composition of the present invention on a seed or bulb, an immersion treatment which comprises immersing a seed for a constant period of time in a solution of the pest controlling composition of the present invention, a film coat treatment, and a pellet coat treatment.

As described above, the pest controlling composition of the present invention can be used in an application to treatment of seed, namely, as a seed treating composition. The present application also includes seed treating compositions containing tolclofos-methyl and the neonicotinoid compounds represented by the formula (1) as active ingredients, such as the pest controlling composition of the present invention. Further, the present application also includes a plant seed treated with tolclofos-methyl and the above-mentioned neonicotinoid compound as active ingredients.

The plant seed of the present invention has usually been treated of an effective amount of tolclofos-methyl and the neonicotinoid compound. Thus, a plant grown from this plant seed can control pests and hardly be suffered from plant diseases.

In the controlling method of the present invention, the application amount of tolclofos-methyl and the neonicotinoid compound represented by the formula (1) can be changed depending on the kind of a plant to be treated, the kind or occurrence of a pest as a target to be controlled, the formulation form, the treatment period, or the weather conditions. The total amount of tolclofos-methyl and the neonicotinoid compound represented by the formula (1) per 10000 $m^2$ (hereinafter, described as the present active ingredient amount) is usually 1 to 5000 g, preferably 2 to 500 g.

The emulsifiable concentrate, wettable powder or flowable is usually diluted with water and sprayed, for performing the treatment. When such a formulation is diluted with water, the concentration of the present active ingredients is in the range of usually 0.0001 to 3 wt %, preferably 0.0005 to 1 wt %. The dust or granules formulation is usually used for the treatment without being diluted.

In the treatment of a seed, the present active ingredient amount per 1 kg of the plant seed is in the range of usually 0.001 to 40 g, preferably 0.01 to 10 g.

The controlling method of the present invention can be used in agricultural lands such as field, paddy field, lawn and orchard or in non-agricultural lands.

The present invention can be used in agricultural lands for cultivating "plants" listed below for controlling pests in the agricultural lands without imparting phytotoxicity to the plants.

Agricultural crops; corn, paddy, wheat, barley, rye, oat, sorghum, cotton, soybean, peanut, buckwheat, beet, rapeseed, sunflower, sugarcane or tobacco, Vegetables; solanaceous vegetables (e.g. eggplant, tomato, green pepper, red pepper or potato), cucurbitaceous vegetables (e.g. cucumber, pumpkin, zucchini, watermelon, melon or squash), brassicaceous vegetables (e.g. radish, turnip, horseradish, kohlrabi, napa cabbage, cabbage, mustard green, broccoli or cauliflower), asteraceous vegetables (e.g. cocklebur, crown daisy, artichoke or lettuce), liliaceous vegetables (e.g. Welsh onion, onion, garlic or asparagus), umbelliferous vegetables (e.g. carrot, parsley, celery or parsnip), chenopodiaceous (e.g. spinach or chard), labiatae vegetables (e.g. Japanese basil, mint or basil), strawberry, sweet potato, Japanese yam, or aroid, Flowers and ornamental plants,
Foliage plant,
Lawn, Fruit trees; pomaceous fruits (e.g. apple, pear, Japanese pear, Chinese quince or quince), stony fruits (e.g. peach, plum, nectarine, Japanese plum, cherry, apricot or prune), citruses (e.g. Satsuma mandarin, orange, lemon, lime or grapefruit), nuts (e.g. chestnut, walnut, hazel, almond, pistachio, cashew nut or macadamia nut), berry fruits (e.g. blue berry, cranberry, blackberry or raspberry), grape, persimmon, olive, loquat, banana, coffee, date, or coconut, Trees other than fruit trees; tea plant, mulberry tree, flowering trees and shrubs, street trees (e.g. Japanese Ash, birch, dogwood, eucalyptus, ginkgo, lilac, maple, oak, poplar, cercis, Formosan sweetgum, platanus, zelkova, Japanese arborvitae, Japanese fir, hemlock fir, juniper, pine, spruce or yew).

The plants include those having resistance to herbicides, for example, an HPPD inhibitor such as isoxaflutole, an ALS inhibitor such as imazethapyr or thifensulfuron-methyl, an EPSP synthesizing enzyme inhibitor, a glutamine synthesizing enzyme inhibitor, an acetyl CoA carboxylase inhibitor, bromoxynil, dicamba, 2,4-D, which resistance is imparted by a classical breeding method or a genetic engineering technique.

Examples of the plant having herbicide resistance imparted by a classical breeding method include rapeseed, wheat, sunflower and paddy, which are resistant to an imidazolinone herbicide such as imazethapyr, and which are available commercially under the trade name of Clearfield. Examples of the plant having herbicide resistance imparted by a classical breeding method include a soybean resistant to a sulfonylurea ALS inhibitor herbicide such as thifensulfuron-methyl, which are available commercially under the trade name of STS soybean. Examples of the plant having herbicide resistance imparted by a classical breeding method include a corn resistant to an acetyl CoA carboxylase inhibitor such as a trione oxime herbicide or an aryloxy phenoxypropionic acid herbicide, which are available commercially under the trade name of SR corn. The plants having resistance to acetyl CoA carboxylase inhibitors are found in, for example, Proc. Natl. Acad. Sci. USA 1990, 87, p. 7175-7179. In addition, a mutant acetyl CoA carboxylase resistant to an acetyl CoA carboxylase inhibitor is known, for example, in Weed Science 53: p. 728-746, 2005. When a gene encoding the mutant acetyl CoA carboxylase is introduced into a plant by a genetic engineering technique or when a mutation related to impartation of resistance is introduced into a gene encoding acetyl CoA carboxylase of a plant, a plant having the resistance to an acetyl CoA carboxylase inhibitor can be produced. Nucleic acids for introduction of a base substitution mutation can be introduced into the cell of a plant by chimeraplasty (see, Gura T. 1999, Repairing the Genome's Spelling Mistakes, Science 285: 316-318) to induce a site-directed amino acid mutation in the gene targeting an acetyl CoA carboxylase inhibitor or herbicide of the plant, and thereby a plant resistant to an acetyl CoA carboxylase inhibitor or herbicide can be produced.

Examples of the plant having herbicide resistance imparted by a genetic engineering technique include corn, soybean, cotton, rapeseed and beet plant varieties which are resistant to glyphosate and which are available commercially under the trade name of RoundupReady or AgrisureGT. Examples of the plant having herbicide resistance imparted by a genetic engineering technique include corn, soybean, cotton and rapeseed varieties which are resistant to glufosinate and which are available commercially under the trade name of LibertyLink. Cottons having herbicide resistance to bromoxynil imparted by a genetic engineering technique are available commercially, for example, under the trade name of BXN.

The plants include those having an ability to produce an insecticidal toxin, for example a selective toxin originated from *Bacillus*, which ability is imparted by a genetic engineering technique.

Examples of the insecticidal toxin which is produced by such a genetically engineered plant include insecticidal proteins derived from *Bacillus cereus* and *Bacillus popilliae*; δ-endotoxins derived from *Bacillus thuringiensis*, such as Cry1Ab, Cry1Ac, Cry1F, Cry1Fa2, Cry2Ab, Cry3A, Cry3Bb1 and Cry9C; insecticidal proteins derived from *Bacillus thuringiensis*, such as VIP 1, VIP 2, VIP 3 and VIP 3A; insecticidal proteins derived from nematodes; toxins produced by animals such as scorpion toxins, spider toxins, bee toxins and insect-specific nerve toxins; fungal toxins; plant lectin; agglutinin; protease inhibitors such as trypsin inhibitors, serine protease inhibitors, patatin, cystatin, and papain inhibitors; ribosome-inactivating proteins (RIP) such as ricin, corn-RIP, abrin, saporin, and briodin; steroid metabolizing enzymes such as 3-hydroxysteroid oxidase, ecdysteroid-UDP-glucosyltransferase, and cholesterol oxidase; ecdysone inhibitors; HMG-CoA reductase; ion channel inhibitors such as sodium channel inhibitors and calcium channel inhibitors; juvenile hormone esterase; diuretic hormone receptors; stilbene synthase; bibenzyl syntase; chitinase; and glucanase.

The insecticidal toxin produced by such a genetically engineered plant also includes hybrid toxins of different insecticidal proteins, for example, selected from δ-endotoxins such as Cry1Ab, Cry1Ac, Cry1F, Cry1Fa2, Cry2Ab, Cry3A, Cry3Bb1 and Cry9C and insecticidal proteins such as VIP 1, VIP 2, VIP 3 and VIP 3A, and toxins in which a part of amino acids constituting an insecticidal protein is deleted or modified. The hybrid toxin is made by combining different domains of the insecticidal proteins by a genetic engineering technique. An example of the toxin in which a part of amino acids constituting an insecticidal protein is deleted includes Cry1Ab in which a part of amino acids is deleted. An example of the toxin in which a part of amino acids constituting an insecticidal protein is modified includes a toxin in which one or more of amino acids of a naturally occurring toxin are substituted.

The insecticidal toxin and the genetically engineered plant having the ability to produce the insecticidal toxin are described, for example, in EP-A-0 374 753, WO 93/07278, WO 95/34656, EP-A-0 427 529, EP-A-451878 or WO 03/052073.

The genetically engineered plant having the ability to produce the insecticidal toxin particularly has resistance to attack by a coleopteran pest, dipteran pest or a lepidopteran pest.

Genetically engineered plants which have one or more pest-resistance genes and thereby produce one or more insecticidal toxins are also known, and some of them are commercially available. Examples of such genetically engineered plants include YieldGard™ (a corn cultivar expressing Cry1Ab toxin), YieldGard Rootworm™ (a corn cultivar expressing Cry3Bb1 toxin), YieldGard Plus™ (a corn cultivar expressing Cry1Ab and Cry3Bb1 toxins), Heculex I™ (a corn cultivar expressing Cry1Fa2 toxin and phosphinothricin N-acetyltransferase (PAT) for imparting resistance to gluphosinate), NuCOTN33B™ (a cotton cultivar expressing Cry1Ac toxin), Bollgard I™ (a cotton cultivar expressing Cry1Ac toxin), Bollgard II™ (a cotton cultivar expressing Cry1Ac and Cry2Ab toxins), VIPCOT™ (a cotton cultivar expressing VIP toxin), NewLeaf™ (a potato cultivar expressing Cry3A toxin), NatureGard Agrisure GT Advantage™ (GA21 glyphosate-resistance character), Agrisure CB Advantage™ (Bt11 corn borer (CB) character), and Protecta™.

The plants include those having an ability to produce an anti-pathogen substance which ability is imparted by a genetic engineering technique.

Examples of the anti-pathogen substance include PR proteins (PRPs, described in EP-A-0 392 225). Such anti-pathogen substances and genetically engineered plants which produce the anti-pathogen substances are described in EP-A-0 392 225, WO 05/33818, EP-A-0 353 191.

Examples of the anti-pathogen substance include ion channel inhibitors such as sodium channel inhibitors, and calcium channel inhibitors (e.g. KP1, KP4, or KP6 toxins produced by viruses); stilbene synthase; bibenzyl synthase; chitinase; PR proteins glucanase; peptide antibiotics; and substances produced by microorganisms such as heterocycle-containing antibiotics, and protein factors involved in plant disease-resistance (described in WO 03/000906).

The "plants" include also those having useful characteristics such as an ability of producing a modified oil component or of producing increased amino acid contents, using a gene recombination technology. Examples thereof include VISTIVE™ (low linolenic soybean having reduced linolenic acid content), and high-lysine (high-oil) corn which has increased lysine or oil content.

Further, also included are stacked plant varieties obtained by combination of some of the classical herbicide activity or herbicide-resistant genes, insecticidal harmful insect-resistant genes, anti-pathogenic substance producing genes, useful characteristics such as an ability of producing a modified oil component or of producing increased amino acid contents.

The pest controlling composition according to the present invention is capable of protecting a plant from offense by pests (for example, harmful arthropods such as harmful insects or harmful mites) performing offense such as eating or sucking on plants described below.

Examples of the pests on which the pest controlling composition according to the present invention exhibits a controlling effect include the following organisms.

Hemiptera harmful insects: Delphacidae such as *Laodelphax striatellus, Nilaparvata lugens*, or *Sogatella furcifera*; Cicadellidae such as *Nephotettix cincticeps*, or *nephotettix virescens*; Aphidoidea such as *Aphis gossypii, Myzus persicae, Brevicoryne brassicae, Macrosiphum euphorbiae, Aulacorthum solani, Rhopalosiphum padi*, or *Toxoptera citricidus*; Stink bugs such as *Nezara antennata, Riptortus clavetus, Leptocorisa chinensis, Eysarcoris parvus, Halyomorpha mista*, or *Lygus lineolaris*; whitefly such as *Trialeurodes vaporariorum, Bemisia tabaci*, or *Bemisia argentifolii*; Coccidea such as *Aonidiella aurantii, Comstockaspis perniciosa, Unaspis citri, Ceroplastes rubens*, or *Icerya purchase*; Tingidae, Psyllidae;

Lepidoptera harmful insects: Pyralidae such as *Chilo suppressalis, Tryporyza incertulas, Cnaphalocrocis medinalis, Notarcha derogata, Plodia interpunctella, Ostrinia furnacalis, Ostrinia nubilaris, Hellula undalis*, or *Pediasia teterrellus*; Coctuidae such as *Spodoptera litura, Spodoptera exigua, Pseudaletiaseparata, Mamestrabrassicae, Agrotisipsilon, Plusia nigrisigna, Trichopulsia* spp., *Heliothis* spp., or *Helicoverpa* spp.; Pieridae such as *Pieris rapae*; Tortricidae such as *Adoxophyes* spp., *Grapholita molesta, Leguminivora glycinivorella, Matsumuraeses azukivora, Adoxophyes orana fasciata, Adoxophyes* SP., *Homona magnanima, Archips fuscocupreanus, Cydia pomonella*, Gracillariiformes such as *Caloptilia theivora*, and *Phyllonorycter ringoneella*; Carposimidae such as *Carposina niponensis*; Lyonetiidae such as *Lyonetia* spp.; Lymantriidae such as *Lymantria* spp., *Euproctis* spp.; Yponomeutidae such as *Plutella xylostella*; Gelechiidae such as *Pectinophora gossypiella*, and *Phthorimaea*

*operculella*; Arctiidae such as *Hyphantria cunea*; Tineidae such as *Tinea translucens, Tineola bisselliella*, etc.;

Thysanoptera harmful insects: Thysanoptera such as *Frankliniella occidentalis, Thrips parmi, Scirtothrips dorsalis, Thrips tabaci, Frankliniella intonsa*, and *Frankliniella fusca*, etc.;

Diptera harmful insects: Liriomyza such as *Musca domestica, Culex popienspallens, Tabanus trigonus, Hylemya antiqua, Hylemya platura, Anopheles sinensis, Agromyza oryzae, Hydrellia griseola, Chlorops oryzae, Liriomyza trifolii; Dacus cucurbitae, Ceratitis capitata;*

Coleopterous harmful insects: *Epilachna vigintioctopunctata, Aulacophora femoralis, Phyllotreta striolata, Oulema oryzae, Echinocnemus squameus, Lissorhoptrus oryzophilus, Anthonomus grandis, Callosobruchus chinensis, Sphenophorus venatus, Popillia japonica, Anomala cuprea, Diabrotica* spp., *Leptinotarsa decemlineata, Agriotes* spp., *Lasioderma serricorne, Anthrenus verbasci, Tribolium castaneum, Lyctus brunneus, Anoplophora malasiaca, Tomicus piniperda;*

Orthopterous harmful insects: *Locusta migratoria, Gryllotalpa africana, Oxya yezoensis, Oxya japonica;*

Hymenopterous harmful insects: *Athalia rosae, Acromyrmex* spp., *Solenopsis* spp.;

Blatodea harmful insects: *Blattella germanica, Periplaneta fuliginosa, Periplaneta americana, Periplaneta brunnea, Blatta orientalis;*

Acarine harmful insects: Tetranichidae such as *Tetranychus urticae, Panonychus citri*, or *Oligonicus* spp.; Eriophidae such as *Aculops pelekassi*; Tarsonemidae such as *Polyphagotarsonemus latus*; Brevipalpus, or Tuckerellidae, Acaridae such as *Tyrophagus putrescentiae*; Pyroglyphidae such as *Dermatophagoides farinae, Dermatophagoides ptrenyssnus*; Cheyletidae such as *Cheyletus eruditus, Cheyletus malaccensis*, or *Cheyletus moorei*, etc.;

Nematode: *Aphelenchoides besseyi*, or *Nothotylenchus acris*.

Among the pests, preferable examples thereof include Aphidoidae, Thysanoptera, Agromyzidae, *Agriotes* spp., *Leptinotarsa decemlineata, Popillia japonica, Anomala cuprea, Anthonomus grandis, Lissorhoptrus oryzophilus, Frankliniella fusca, Diabrotica* spp., *Plutella xylostella, Pieris rapae* and *Leguminivora glycinivorella.*

When tolclofos-methyl and the neonicotinoid compound as explained above are applied in an effective amount to a plant or a soil for cultivating the plant according to the pest controlling method of the present invention, a plant disease can be controlled.

The present application also includes a plant disease controlling composition containing tolclofos-methyl and the neonicotinoid compound as active ingredients and a plant disease controlling method which comprises applying tolclofos-methyl and the neonicotinoid compound in an effective amount to a plant or a soil for cultivating the plant.

In the plant disease controlling composition, the total amount of tolclofos-methyl and the neonicotinoid compound is in the range of usually 0.1 to 99 wt %, preferably 0.2 to 90 wt %. The plant disease controlling composition can be prepared in the same manner as for the pest controlling composition.

In the plant disease controlling method, application of tolclofos-methyl and the neonicotinoid compound can be carried out in the same manner as in the pest controlling method.

The plant disease controlling composition is effective also for the following plant diseases.

Paddy diseases: *Magnaporthe grisea, Cochliobolus miyabeanus, Rhizoctonia solani, Gibberella fujikuroi.*

Wheat diseases: *Erysiphe graminis, Fusarium graminearum* (*F. avenacerum, F. culmorum, Microdochium nivale*), *Puccinia striiformis* (*p. graminis, p. recondita*), *Micronectriella nivale, Typhula* SP., *Ustilago tritici, Tilletia caries, Pseudocercosporella herpotrichoides, Mycosphaerella graminicola, Stagonosporanodorum, Pyrenophora tritici-repentis.*

Barley diseases: *Erysiphe graminis, Fusarium graminearum* (*F. avenacerum, F. culmorum, Microdochium nivale*), *Puccinia striiformis* (*P. graminis, P. hordei*), *Ustilago nuda, Rhynchosporium secalis, Pyrenophora teres, Cochliobolus sativus, Pyrenophora graminea, Rhizoctonia solani.*

Corn diseases: *Ustilago maydis, Cochliobolus heterostrophus, Gloeocercospora sorghi, Puccinia polysora, Cercospora zeaemaydis, Rhizoctonia solani.*

Citrus diseases: *Diaporthe citri, Elsinoe fawcetti, Penicillium digitatum* (*P. italicum*), *Phytophthora parasitica*(*Phytophthora citrophthora*).

Apple diseases: *Monilinia mali, Valsa ceratosperma, Podosphaera leucotricha*, Alternariaalternata apple pathotype, *Venturia inaequalis, Colletotrichum acutatum, Phytophtora cactorum, Diplocarpon mali, Botryosphaeria berengeriana.*

Pear diseases: *Venturia nashicola* (*V. pirina*), *Alternaria alternata* Japanese pear pathotype, *Gymnosporangium haraeanum, Phytophtora cactorum.*

Peach diseases: *Monilinia fructicola, Cladosporium carpophilum, Phomopsis* SP.

Grape diseases: *Elsinoe ampelina, Glomerella cingulata, Uncinula necator, Phakopsora ampelopsidis, Guignardia bidwellii, Plasmopara viticola.*

Persimmon diseases: *Gloeosporium kaki, Cercospora kaki* (*Mycosphaerella nawae*).

Gourd diseases: *Colletotrichum lagenarium, Sphaerotheca fuliginea, Mycosphaerella melonis, Fusarium oxysporum, Pseudoperonospora cubensis, Phytophthora* SP., *Pythium* SP.;

Tomato diseases: *Alternaria solani, Cladosporium fulvum, Phytophthora infestans*

Eggplant diseases: *Phomopsis vexans, Erysiphe cichoracearum.*

Brassicaceous vegetable diseases: *Alternaria japonica, Cercosporella brassicae, Plasmodiophora brassicae, Peronospora parasitica.*

Welsh onion diseases: *Puccinia allii, Peronospora destructor.*

Soybean diseases: *Cercospora kikuchii, Elsinoe glycines, Diaporthe phaseolorum* var. *sojae, Septoria glycines, Cercospora sojina, Phakopsora pachyrhizi, Phytophthora sojae, Rhizoctonia solani.*

Kidney bean diseases: *Colletotrichum lindemthianum.*

Peanut diseases: *Cercospora personata, Cercospora arachidicola, Sclerotium rolfsii.*

Pea diseases: *Erysiphe pisi, Fusarium solani* F. SP. *Pisi.*

Potato diseases: *Alternaria solani, Phytophthora infestans, Phytophthora erythroseptica, Spongospora subterranean* f. sp. *subterranea, Rhizoctonia solani.*

Strawberry diseases: *Sphaerotheca humuli, Glomerella cingulata.*

Tea plant diseases: *Exobasidium reticulatum, Elsinoe leucospila, Pestalotiopsis* SP., *Colletotrichum theaesinensis.*

Tobacco diseases: *Alternaria longipes, Erysiphe cichoracearum, Colletotrichum tabacum, Peronospora tabacina, Phytophthora nicotianae.*

Rapeseed diseases: *Sclerotinia sclerotiorum, Rhizoctonia solani.*

Cotton diseases: *Rhizoctonia solani*.

Beet diseases: *Cercospora beticola, Thanatephorus cucumeris, Thanatephorus cucumeris, Aphanomyces cochlioides*.

Rose diseases: *Diplocarpon rosae, Sphaerotheca pannosa, Peronospora sparsa*.

Diseases of chrysanthemum and asteraceae: *Bremia lactucae, Septoria chrysanthemi-indici, Puccinia horiana*.

Diseases of various plants: *Pythium aphanidermatum (Pythium debarianum, Pythium graminicola, Pythium irregulare, Pythium ultimum), Botrytis cinerea, Sclerotinia sclerotiorum, Sclerotium rolfsii*.

Radish diseases: *Alternaria brassicicola*.

Lawn diseases: *Sclerotinia homeocarpa, Rhizoctonia solani*.

Banana diseases: *Mycosphaerella fijiensis (Mycosphaerella musicola)*.

Sunflower diseases: *Plasmopara halstedii*.

Seed diseases or diseases in the initial stage of growth of various plants caused by *Aspergillus* spp., *Penicillium* spp., *Fusarium* spp., *Gibberella* spp., *Tricoderma* spp., *Thielaviopsis* spp., *Rhizopus* spp., *Mucor* spp., *Corticium* spp., *Phoma* spp., *Rhizoctonia* spp., or *Diplodia* spp.

Virus diseases of various plants mediated by *Polymixa* spp., and *Olpidium* spp.

When the plant disease controlling composition of the present invention is used in a spraying treatment, a high controlling effect is expected on plant diseases occurring particularly in wheat, barley, corn, soybean, cotton, rapeseed, grape, lawn or apple among the plants. Of these plant diseases occurring in plants, those in which a particularly high effect is expected include wheat: *Mycosphaerella graminicola, Pyrenophora tritici-repentis, Mycrodochium nivale, Rhizoctonia solani*, and *Pseudocercosporella herpotrichoides*, barley: *Pyrenophora teres, Cochliobolus sativus, Pyrenophora graminea, Ustilago tritici (U. nuda), Tilletia caries*, and *Rhynchosporium secalis*, corn: *Cochliobolus heterostrophus*, and *Cercospora zeae-maydis*, soybean: *Cercospora kikuchii*, and *Septoria glycines*, cotton: *Rhizoctonia solani*, rapeseed: *Rhizoctonia solani*, and *Sclerotinia sclerotiorum*, grape: *Botrytis cinerea*, lawn: *Sclerotinia homeocarpa*, and *Rhizoctonia solani*, apple: *Venturia inaequalis*.

When the plant disease controlling composition of the present invention is used in a seed treatment, a high controlling effect is expected on plant diseases occurring particularly in corn, sorghum, paddy, rapeseed, soybean, potato, beet and cotton among the plants. Of these plant diseases occurring in plants, those in which a particularly high effect is expected include *Rhizoctonia solani*, diseased caused by *Pythium*, and diseases caused by *Fusarium*.

EXAMPLES

The present invention will be illustrated further in detail by formulation examples, seed treating examples and test examples below, but the present invention is not limited only to the following examples. In the following examples, parts are by weight unless otherwise stated.

Formulation Example 1

Five (5) parts of clothianidin, 5 parts of tolclofos-methyl, 35 parts of a mixture (weight ratio 1:1) of white carbon and polyoxyethylene alkyl ether sulfate ammonium salt and 55 parts of water are mixed. The mixture as obtained is finely pulverized by a wet pulverization method to give a flowable formulation.

Formulation Example 2

An aqueous solution containing 5 parts of imidacloprid, 10 parts of tolclofos-methyl, 1.5 parts of sorbitan trioleate and 2 parts of polyvinyl alcohol is prepared by mixing these components. The solution (28.5 parts) is finely pulverized by a wet pulverization method. Then 45 parts of an aqueous solution containing 0.05 parts of xanthan gum and 0.1 part of aluminum magnesium silicate are added thereto, 10 parts of propylene glycol is subsequently added and then the resultant mixture is stirred to give a flowable formulation.

Formulation Example 3

An aqueous solution containing 5 parts of thiamethoxam, 20 parts of tolclofos-methyl, 1.5 parts of sorbitan trioleate and 2 parts of polyvinyl alcohol is prepared by mixing these components. The solution (28.5 parts) is finely pulverized by a wet pulverization method. Then 35 parts of an aqueous solution containing 0.05 parts of xanthan gum and 0.1 part of aluminum magnesium silicate are added thereto, and 10 parts of propylene glycol is subsequently added and then the resultant mixture is stirred to give a flowable formulation.

Formulation Example 4

Mixed are 40 parts of imidacloprid, 5 parts of tolclofos-methyl, 5 parts of propylene glycol (manufactured by Nacalai Tesque Inc.), 5 parts of Soprophor FLK (manufactured by Rhodia Nikka), 0.2 parts of anti-foam C emulsion (manufactured by Dow Corning), 0.3 parts of Proxel GXL (manufactured by Arch Chemicals, Inc.) and 44.5 parts of ion exchanged water in this ratio, to prepare a slurry. To 100 parts of the slurry is added 150 parts of glass beads (diameter: 1 mm), and the mixture is pulverized for 2 hours while being cooled with cooling water. After pulverization, the glass beads are removed by filtration to give a flowable formulation.

Formulation Example 5

Mixed are 50 parts of thiamethoxam, 0.5 parts of tolclofos-methyl, 38 parts of NN kaolin clay (manufactured by Takehara Chemical Industrial Co., Ltd.), 10 parts of Morwet D425 and 1.5 parts of Morwer EFW (manufactured by AkzoNobel) in this ratio, to give an AI premix. This premix is pulverized by jet mill to give a dust.

Formulation Example 6

One (1) part of clothianidin, 4 parts of tolclofos-methyl, 1 part of synthetic hydrated silicon oxide, 2 parts of calcium ligninsulfonate, 30 parts of bentonite and 62 parts of kaolin clay are thoroughly pulverized and mixed. Water is added thereto and the mixture is thoroughly kneaded, then granulated and dried to give a granule.

Formulation Example 7

One (1) part of imidacloprid, 40 parts of tolclofos-methyl, 3 parts of calcium ligninsulfonate, 2 parts of sodium laurylsulfate and 54 parts of synthetic hydrated silicon oxide are thoroughly pulverized and mixed to give a wettable powder.

Formulation Example 8

One (1) part of thiamethoxam, 2 parts of tolclofos-methyl, 87 parts of kaolin clay and 10 parts of talc are thoroughly pulverized and mixed to give a dust.

Formulation Example 9

Two (2) parts of imidacloprid, 0.25 parts of tolclofos-methyl, 14 parts of polyoxyethylene styryl phenyl ether, 6 parts of calcium dodecylbenzenesulfonate and 77.75 parts of xylene are thoroughly mixed to give an emulsifiable concentrate.

Formulation Example 10

An aqueous solution containing 10 parts of clothianidin, 2.5 parts of tolclofos-methyl, 1.5 parts of sorbitan trioleate and 2 parts of polyvinyl alcohol is prepared by mixing these components. Thirty (30) parts of the solution are finely pulverized by a wet pulverization method. Then 46 parts of an aqueous solution containing 0.05 parts of xanthan gum and 0.1 part of aluminum magnesium silicate are added thereto, 10 parts of propylene glycol is subsequently added thereto, and the resultant mixture is stirred to give a flowable formulation.

Formulation Example 11

One (1) part of clothianidin, 20 parts of tolclofos-methyl, 1 part of synthetic hydrated silicon oxide, 2 parts of calcium ligninsulfonate, 30 parts of bentonite and 47 parts of kaolin clay are thoroughly pulverized and mixed, water is added to thereto. The mixture as obtained is thoroughly kneaded, granulated and then dried to give a granule.

Formulation Example 12

Forty (40) parts of thiamethoxam, 1 part of tolclofos-methyl, 3 parts of calcium ligninsulfonate, 2 parts of sodium laurylsulfate and 54 parts of synthetic hydrated silicon oxide are thoroughly pulverized and mixed to give a wettable powder.

Formulation Example 13

One (1) part of tolclofos-methyl, 20 parts of clothianidin and 79 parts of acetone are mixed in this ratio, to give an emulsifiable concentrate.

Formulation Example 14

Mixed are 73 parts of tolclofos-methyl, 9 parts of clothianidin and 18 parts of acetone in this ratio to give an emulsifiable concentrate.

Seed Treating Example 1

Ten (10) kg of rapeseed dry seeds are coated with 50 ml of a flowable formulation produced according to Formulation Example 1 using a rotation mode seed treating machine (Seed Dresser, manufactured by Hans-Ulrich Hege GmbH), to give treated seeds.

Seed Treating Example 2

Ten (10) kg of corn dry seeds are coated with 40 ml of a flowable formulation produced according to Formulation Example 2 using a rotation mode seed treating machine (Seed Dresser, manufactured by Hans-Ulrich Hege GmbH), to give treated seeds.

Seed Treating Example 3

Five (5) parts of a flowable formulation produced according to Formulation Example 3, 5 parts of Pigment BPD6135 (manufactured by Sun Chemical) and 35 parts of water are blended to prepare a blend. Ten (10) kg of paddy dry seeds are coated with 60 ml of the blend using a rotation mode seed treating machine (Seed Dresser, manufactured by Hans-Ulrich Hege GmbH), to give treated seeds.

Seed Treating Example 4

Ten (10) kg of corn dry seeds are dust-coated with 50 g of a dust produced according to Formulation Example 4, to give treated seeds.

Seed Treating Example 5

Ten (10) kg of soybean dry seeds are coated with 50 ml of a flowable formulation produced according to Formulation Example 1 using a rotation mode seed treating machine (Seed Dresser, manufactured by Hans-Ulrich Hege GmbH), to give treated seeds.

Seed Treating Example 6

Ten (10) kg of wheat dry seeds are coated with 50 ml of a flowable formulation produced according to Formulation Example 2 using a rotation mode seed treating machine (Seed Dresser, manufactured by Hans-Ulrich Hege GmbH), to give treated seeds.

Seed Treating Example 7

Five (5) parts of a flowable formulation produced according to Formulation Example 3, 5 parts of Pigment BPD6135 (manufactured by Sun Chemical) and 35 parts of water are blended. Then 10 kg of potato rootstalk pieces are coated with 70 ml of the blend using a rotation mode seed treating machine (Seed Dresser, manufactured by Hans-Ulrich Hege GmbH), to give treated seeds.

Seed Treating Example 8

Five (5) parts of a flowable produced according to Formulation Example 3, 5 parts of Pigment BPD6135 (manufactured by Sun Chemical) and 35 parts of water are blended. Then 10 kg of sunflower seeds are coated with 70 ml of the resultant blend using a rotation mode seed treating machine (Seed Dresser, manufactured by Hans-Ulrich Hege GmbH), to give treated seeds.

Seed Treating Example 9

Ten (10) kg of cotton dry seeds are dust-coated with 40 g of a dust produced according to Formulation Example 5, to give treated seed.

Seed Treating Example 10

Five (5) g of cucumber seeds are coated with 1 ml of an emulsifiable concentrate produced according to Formulation Example 13 using a rotation mode seed treating machine (Seed Dresser, manufactured by Hans-Ulrich Hege GmbH), to give treated seeds.

Test Example 1

Thoroughly mixed were 2.5 parts of clothianidin, 1.25 parts of tolclofos-methyl, 14 parts of polyoxyethylene styryl phenyl ether, 6 parts of calcium dodecylbenzenesulfonate and 76.25 parts of xylene to give a formulation.

The formulation was diluted with acetone, to prepare an acetone mixed solution containing clothianidin and tolclofos-methyl of given concentration.

Five (5) g of cucumber (Sagami Hanjiro) seeds were coated with 1 ml of the mixed solution using a rotation mode seed treating machine (Seed Dresser, manufactured by Hans-Ulrich Hege GmbH), to give treated seeds.

The treated seeds were allowed to stand still overnight, then, sowed on a soil stuffed in a plastic pot, and covered by a soil blended with *Rhizoctonia solani* cultured in a bran medium. Cultivation thereof was performed at room temperature while irrigating. Seven (7) days after sowing, the number of non-budded seeds was checked, and the damaged ratio was calculated from the formula 1. Based on the damaged ratio, the control value was calculated from the formula 2.

For comparison, an acetone solution containing clothianidin of a given concentration, and an acetone solution containing tolclofos-methyl of a given concentration were prepared, and subjected to the same test.

Damaged ratio=(number of non-budded seeds and number of diseased seedling)×100/(total sowed number)     "Formula 1"

Control value=$100 \times (A-B)/A$     "Formula 2"

A: damaged ratio of plant in non-drug treated area
B: damaged ratio of plant in treated area
The results are shown in Table 1.

| Test compound | Active ingredient amount (g/100 kg-seed) | Control value |
|---|---|---|
| Clothianidin + tolclofos-methyl | 200 + 10 | 83 |
| Clothianidin | 200 | 4 |
| Tolclofos-methyl | 10 | 57 |

Test Example 2

The formulation described in Formulation Example 13 is diluted with acetone to prepare an acetone mixed solution containing clothianidin and tolclofos-methyl. Corn seeds are coated with the acetone mixed solution using a rotation mode seed treating machine (Seed Dresser, manufactured by Hans-Ulrich Hege GmbH), to give treated seeds.

The treated seeds are allowed to stand still overnight, then, sowed on a soil stuffed in a plastic pot, and covered by a soil blended with *Rhizoctonia solani* separately cultured in a bran medium. Cultivation thereof is performed at room temperature while irrigating. Ten (10) days after sowing, the number of non-budded seeds is checked. The damaged ratio is calculated from the "formula 1". The control value is calculated from the "formula 2". According to the seed treating method of the present invention, an excellent controlling effect is obtained.

Test Example 3

In a polyethylene cup, a soybean is planted, and allowed to grow until the first true leaves are developed. About 20 insects of *Aulacorthum solani* are parasitized there.

A wettable powder of tolclofos-methyl and a wettable powder of clothianidin are diluted with water separately, then mixed in a tank to prepare a tank mix solution containing tolclofos-methyl and clothianidin. One day after, the tank mix solution is sprayed in a proportion of 20 ml/cup onto the soybean. Six days after spraying, the number of *Aulacorthum solani* is checked, and the control value is calculated by the following formula.

Control value=$\{1-(Cb \times Tai)/(Cai \times Tb)\} \times 100$

Letters in the formula have the following meanings.
Cb: insect number before treatment in non-treated area
Cai: insect number in observation in non-treated area
Tb: insect number before treatment in treated area
Tai: insect number in observation in treated area Test Example 4

One particle of corn (Pioneer) seed was coated with 5 μl of the emulsifiable concentrate produced according to Formulation Example 14 in a 15 ml centrifugal tube. The resultant treated seed was sowed on a 1/10000 a Wagner pot. It was allowed to grow for 9 days at temperature of 23° C. in the greenhouse, and then 5 insects of *Rhopalosiphum padi* were released. Five days after insect releasing, the number of *Rhopalosiphum padi* was checked. The control value was calculated from the following formula.

Control value=$\{1-(\text{insect number in treated area/insect number in non-treated area})\} \times 100$ As a result, the control value in the treated area was 100, obtaining an excellent effect.

INDUSTRIAL APPLICABILITY

The present invention is capable of providing a pest controlling composition having high activity, a method which can effectively controls a pest, and the like.

The invention claimed is:

1. A pest controlling composition comprising tolclofos-methyl and a neonicotinoid compound selected from the group consisting of clothianidin, thiamethoxam, nitenpyram, dinotefuran, acetamiprid and thiacloprid;
    wherein the weight ratio of tolclofos-methyl to the neonicotinoid compound is in the range of 0.004:1 to 100:1.

2. The pest controlling composition according to claim 1, wherein the neonicotinoid compound is selected from the group consisting of clothianidin and thiamethoxam.

3. A seed treating composition comprising tolclofos-methyl and the neonicotinoid compound as defined in claim 1 as active ingredients.

4. A plant seed treated with an effective amount of tolclofos-methyl and the neonicotinoid compound as defined in claim 1.

5. A pest controlling method which comprises applying tolclofos-methyl and the neonicotinoid compound as defined in claim 1 as active ingredients to a pest, a plant or a soil for cultivating the plant.

6. The pest controlling composition according to claim 1, wherein the neonicotinoid compound is selected from the group consisting of thiamethoxam, nitenpyram, dinotefuran, acetamiprid and thiacloprid.

* * * * *